United States Patent
Yoshida

(10) Patent No.: US 8,086,014 B2
(45) Date of Patent: Dec. 27, 2011

(54) X-RAY IMAGE DIAGNOSTIC APPARATUS AND CONTROL METHOD, AND IMAGE PROCESSING METHOD

(75) Inventor: Takashi Yoshida, Yokosuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 389 days.

(21) Appl. No.: 12/471,848

(22) Filed: May 26, 2009

(65) Prior Publication Data

US 2009/0304254 A1  Dec. 10, 2009

(30) Foreign Application Priority Data

Jun. 10, 2008 (JP) ................................ 2008-152258

(51) Int. Cl.
*G06K 9/00* (2006.01)

(52) U.S. Cl. .................................................... 382/132

(58) Field of Classification Search .................. None
See application file for complete search history.

(56) References Cited

U.S. PATENT DOCUMENTS

| 6,920,238 B1 * | 7/2005 | Chen et al. ................. 382/128 |
| 7,209,592 B2 * | 4/2007 | Keller et al. ................ 382/240 |
| 7,602,981 B2 * | 10/2009 | Niwa et al. ................. 382/239 |

FOREIGN PATENT DOCUMENTS

| JP | 1-189772 | 7/1989 |
| JP | 6-209926 | 8/1994 |

* cited by examiner

*Primary Examiner* — Tu Nguyen
(74) *Attorney, Agent, or Firm* — Fitzpatrick, Cella, Harper & Scinto

(57) ABSTRACT

The present invention implements efficient transmission of captured images while also maintaining high-resolution image quality. The present invention is an image processing method for an X-ray image diagnosis apparatus, the method including the steps of: obtaining the effective bandwidth for transmitting captured images; obtaining imaging conditions; calculating the respective resulting data amounts when a captured image captured under the conditions is compressed using lossless and lossy compression, mixing the captured images compressed losslessly and lossily, and determining the mix ratio so that the transmission amount per unit of time when multiple captured images are transmitted is less than the effective bandwidth; and transmitting the multiple captured images compressed losslessly and lossily at the determined ratio.

8 Claims, 8 Drawing Sheets

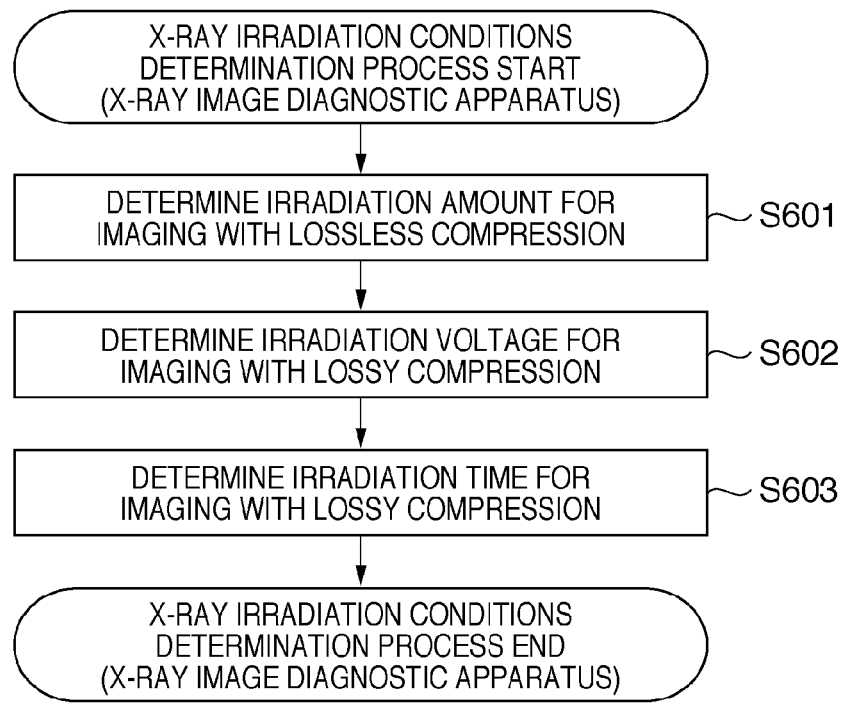
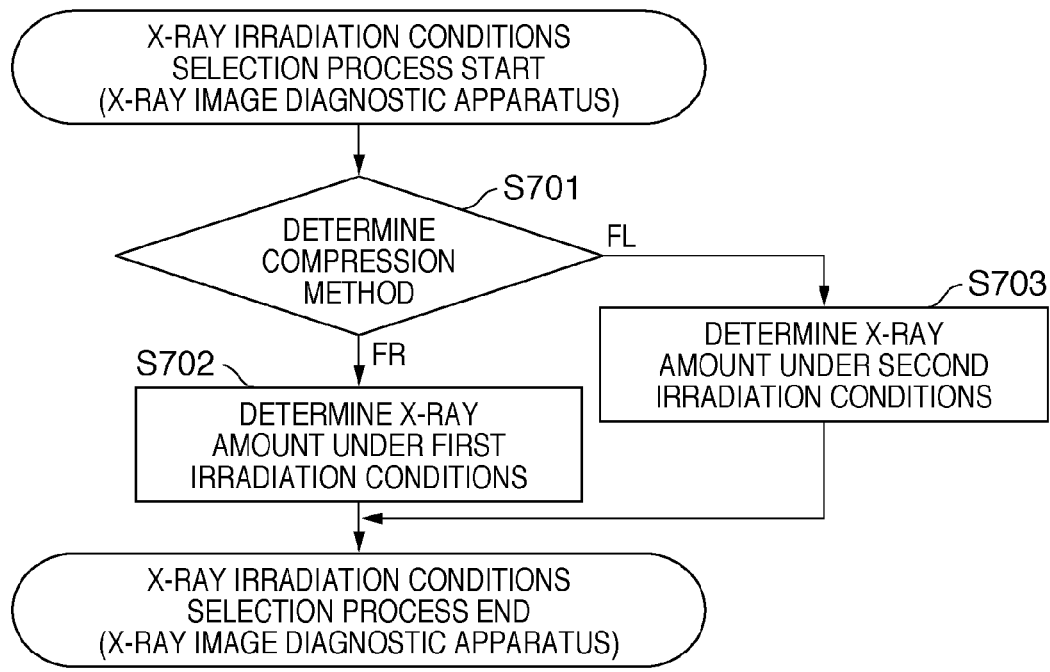

X-RAY IMAGE DIAGNOSTIC APPARATUS AND CONTROL METHOD, AND IMAGE PROCESSING METHOD

BACKGROUND OF THE INVENTION

1. Field of the Invention

The present invention relates to an image processing technique for processing images captured by an X-ray image diagnostic apparatus.

2. Description of the Related Art

Imaging systems using photomultipliers as X-ray detection units have hitherto been widely utilized as X-ray image diagnostic apparatuses for making medical diagnoses. Such imaging systems, in which a captured image that has undergone phototransformation in such a photomultiplier is processed in analog form and displayed in a monitor, are called "analog image intensifiers".

However, X-ray image diagnostic apparatuses utilizing digital X-ray imaging systems that digitally detect X-rays and form captured images (called "digital X-ray image diagnostic apparatuses" hereinafter) are becoming more common as of late, taking the place of such analog image intensifiers.

An apparatus that uses a flat panel detector (abbreviated as "FPD" hereinafter) as its detection device can be given as a representative example of a digital X-ray image diagnostic apparatus.

FPDs are provided with units configured of, for example, solid-state image sensors having high X-ray sensitivity that convert detected X-rays into electrical signals based on their intensity, and output the electrical signals. Alternatively, the FPDs are provided with units that combine a scintillator, which absorbs the energy of the X-rays and emits fluorescent light of an intensity in accordance therewith, with a photoelectric conversion element, which has a high sensitivity to visible light and converts that light into electrical signals based on the intensity thereof. The FPDs are provided with such units as well as A/D converters that digitize the analog signals from those units.

Digital X-ray image diagnostic apparatuses that use such FPDs are capable of realizing wider dynamic ranges and obtaining higher-resolution images than X-ray image diagnostic apparatuses that use conventional analog image intensifiers. Recently, digital X-ray image diagnostic apparatuses are also showing properties that are not inferior to conventional image intensifiers in terms of frame rates when capturing moving pictures.

Furthermore, because digital X-ray image diagnostic apparatuses enable the captured images to be handled in digital form, they allow more advanced image processing to be performed, without drops in image quality during processing, transmission, and storage.

The spread of digital X-ray image diagnostic apparatuses can therefore contribute to improvements in the accuracy of diagnoses due to the higher image quality. Such apparatuses can also contribute to the implementation of new types of medical systems, such as data management facilitated by the digital nature of the images, links with other medical devices through digital networking, and so on.

Recently, remote medical services are garnering attention as one such new medical system.

In the past, it has been difficult to perform emergency medical procedures, perform examinations and treat problems using advanced devices, and so on in regions that are unable to obtain specialized medical care, such as remote islands that lack general hospitals. Therefore, when emergency medical care is necessary in such regions, doctors working outside of their specialization generally provide the initial care, after which the patient is transported to a general hospital capable of more advanced medical care. However, it often takes time to select the hospital to transport the patient to, and to actually transport the patient to that hospital.

In light of this, if a communication path capable of transferring data between clinics on remote island and general hospitals in larger cities could be laid and remote medical services provided, captured images obtained using an X-ray image diagnostic apparatus on the island could be viewed by specialists in a general hospital.

Implementing remote medical services using such an X-ray image diagnosis system makes it possible to obtain high-level examination/treatment services under the instruction of a specialist even in regions that lack advanced medical facilities.

It goes without saying that when implementing such a remote medical service, it is necessary for the transmitted captured images to be of a quality sufficient for diagnosis and treatment, and it is particularly necessary, in terms of diagnostic performance, for the image resolution to be sufficiently high. At the same time, it is particularly necessary, when making diagnoses and performing treatment using moving pictures, to ensure a frame rate sufficient for making diagnostic and treatment instructions.

However, there are often constraints on the transmission bandwidth that can actually be used, and in light of this, it is necessary to efficiently encode captured images in order to reduce the data amount thereof before transmitting the images. However, because the captured images are used for diagnoses and treatment, excessive compression coding leading to a drop in image quality is unacceptable.

Therefore, when implementing such a remote medical service, it is important to efficiently transmit captured images of the required quality within the effective bandwidth for transmission (in other words, to implement efficient transmission while also maintaining high-resolution image quality).

Selectively changing the method used to encode the captured images is useful as a way to implement efficient transmission while also maintaining high-resolution image quality in such a manner. Japanese Patent Laid-Open Nos. 06-209926 and 01-189772 (hereinafter referred to as Patent Documents 1 and 2 respectively) are known as techniques for selectively changing the method used to encode captured images.

Patent Document 1 discloses a configuration that changes the amount of data obtained (frame rate, X-ray amount) and the compression coding method depending on whether a region is a specified region of interest or not. Patent Document 2, meanwhile, discloses a configuration that detects biological changes and changes the compression coding method based on the detected changes. In Patent Document 2, frames considered more important in terms of biological changes are encoded using a lossless compression method, whereas other frames are encoded efficiently using a lossy compression method.

However, the configurations disclosed in Patent Documents 1 and 2 are not intended to implement remote medical services, and do not aim to control encoding captured images within the effective bandwidth for transmission. Therefore, applying such configurations as-is to a remote medical service may result in the data amount exceeding the effective bandwidth for transmission.

To be more specific, with Patent Document 1, the effects of the compression coding are reliable when parts necessary for diagnosis and parts unnecessary for diagnosis coexist within the same frame. However, this technique is ineffective when, for example, irradiating only an area of interest with X-rays and not imaging the other areas in order to reduce the amount of X-ray irradiation as much as possible, as with radioscopy imaging.

Meanwhile, Patent Document 2 changes the compression coding method based on time, as opposed to Patent Document 1, which changes the compression coding method based on space; thus a certain degree of effectiveness can be expected. However, because the data amount depends on biological changes, there is no guarantee that that data amount will fall within the effective bandwidth for transmission.

SUMMARY OF THE INVENTION

The present invention has been conceived in light of the abovementioned problems.

An X-ray image diagnostic apparatus according to the present invention is configured as follows. That is, the X-ray image diagnostic apparatus irradiates a subject with X-rays and transmits multiple captured images obtained by imaging the subject to a control apparatus, and includes: a first calculation unit configured to calculate the transmission amount that can be transmitted per unit of time; an obtainment unit configured to obtain conditions, out of the imaging conditions present when imaging the subject, that relate to the data amount of each captured image and the number of captured images captured per unit of time; a second calculation unit configured to calculate the respective resulting data amounts when a captured image captured under the conditions obtained by the obtainment unit is compressed at first and second compression rates; a determination unit configured to mix the captured images compressed using the first and second compression rates and determine the mix ratio so that the transmission amount per unit of time when the multiple captured images are transmitted is less than the transmission amount calculated by the first calculation unit; and a transmission unit configured to transmit the multiple captured images compressed using the first and second compression rates at the ratio determined by the determination unit.

According to the present invention, it is possible to provide an image processing technique, favorable for application in a remote medical service implemented using an X-ray image diagnosis system, that is capable of implementing efficient transmission of captured images while also maintaining high-resolution image quality.

Further features of the present invention will become apparent from the following description of an exemplary embodiment (with reference to the attached drawings).

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 6 is a flowchart illustrating the detailed flow of an X-ray irradiation condition determination process (step S404).

FIG. 7 is a flowchart illustrating the detailed flow of an X-ray irradiation condition selection process (step S406).

DESCRIPTION OF THE EMBODIMENTS

Embodiments of the present invention shall now be described in detail in accordance with the accompanying drawings.

First Embodiment

<1. Configuration of X-Ray Image Diagnosis System>

Figure 1:
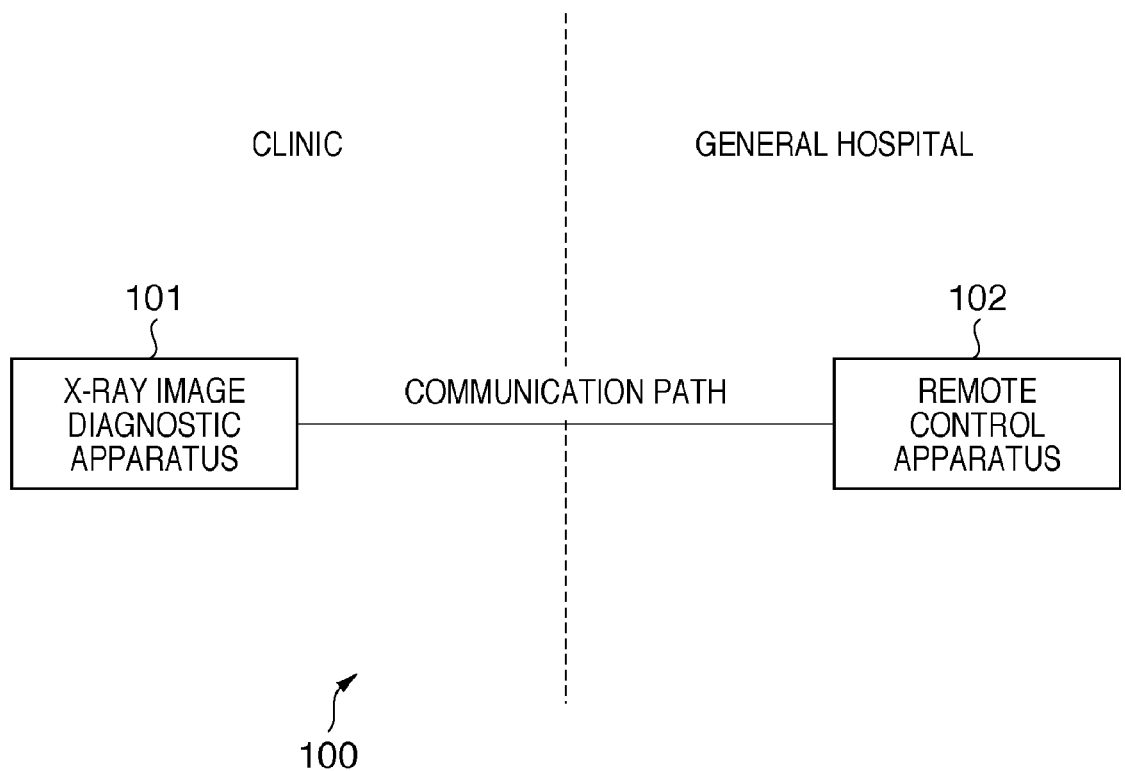
FIG. 1 is a diagram illustrating the overall configuration of an X-ray image diagnosis system according to a first embodiment of the present invention.

FIG. 1 is a diagram illustrating the overall configuration of an X-ray image diagnosis system according to a first embodiment of the present invention. As shown in FIG. 1, an X-ray image diagnosis system 100 according to the present embodiment includes an X-ray image diagnostic apparatus 101 and a remote control apparatus 102. The X-ray image diagnostic apparatus 101 is installed in, for example, a clinic on a remote island, whereas the remote control apparatus 102 is installed in, for example, a general hospital, and the two apparatuses are connected to each other via a communication path, and are thus capable of communicating with each other.

This makes it possible to use the remote control apparatus 102 to operate the X-ray image diagnostic apparatus 101 remotely, display and record images captured by the X-ray image diagnostic apparatus 101, and so on.

<2. Configuration of X-Ray Image Diagnostic Apparatus>

Figure 2:
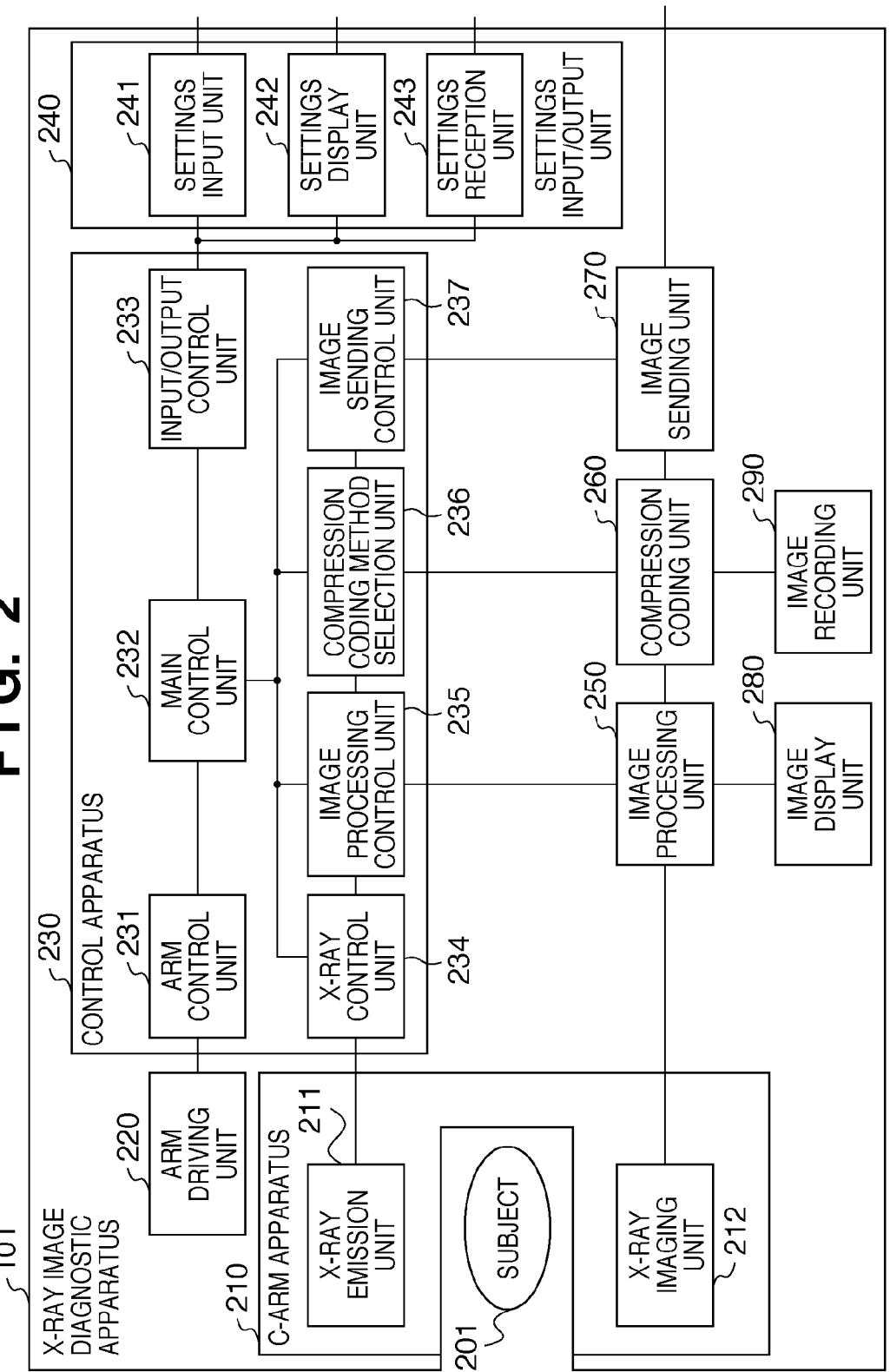
FIG. 2 is a diagram illustrating the internal configuration of an X-ray image diagnostic apparatus 101.

FIG. 2 is a diagram illustrating the internal configuration of the X-ray image diagnostic apparatus 101. Although the X-ray image diagnostic apparatus 101 is described in the present embodiment as being a C-arm X-ray image diagnostic apparatus, it should be noted that the present invention is not limited thereto.

In FIG. 2, 210 is a C-arm apparatus, with an X-ray emission unit 211 provided on one end thereof and an X-ray imaging unit 212 provided on the other end thereof; X-rays irradiated by the X-ray emission unit 211 permeate a subject 201 and are detected by the X-ray imaging unit 212.

Conventionally, an analog image intensifier has primarily been used as the X-ray imaging unit 212, but recently, it is more common to use a flat panel detector (FPD).

The C-arm apparatus 210 is capable of movement and rotation based on the purpose of the examination, the area to be imaged, and so on, and the X-ray image diagnostic apparatus 101 includes an arm driving unit 220 for driving the C-arm apparatus 210.

230 is a control apparatus that controls the overall X-ray image diagnostic apparatus 101 based on inputted information regarding the subject 201, settings made for imaging conditions, and so on. Details of the control apparatus 230 shall be described later.

240 is a settings input/output unit that functions as an interface for accepting, from an input device provided in the X-ray image diagnostic apparatus 101 or from the remote control apparatus 102, information regarding the subject 201 and imaging condition settings, or operations to be performed by the X-ray image diagnostic apparatus 101.

The settings input/output unit 240 includes a settings input unit 241 that accepts information regarding the subject 201, imaging condition settings, and so on. The settings input/output unit 240 also includes a settings display unit 242 for displaying various setting values set through the settings input unit 241, the status of the X-ray image diagnostic apparatus, and so on. The settings input/output unit 240 further includes a settings reception unit 243 for receiving setting values set through the remote control apparatus 102.

The settings input unit 241 is realized using illuminated switches, a touch-panel liquid-crystal display, or the like. The illuminated switches are realized using hand-operated switches, foot pedals, and so on. The settings display unit 242 is also realized using, for example, a display or the like.

250 is an image processing unit that processes images into a form suited for diagnosis/interpretation by performing noise removal processing and the like on the captured images obtained by the X-ray imaging unit 212.

260 is a compression coding unit that encodes the captured images processed by the image processing unit 250 into a form suitable for transmission. In the present embodiment, the compression coding unit 260 is provided with functionality for switching between lossless compression processing and lossy compression processing on a captured image-by-captured image basis (that is, at the frame level).

270 is an image sending unit that transmits captured images encoded by the compression coding unit 260 using a predetermined communication protocol. The transmitted captured images are received by the remote control apparatus 102 using a receiving unit 340 provided therein. Although the present embodiment uses a protocol such as TCP/IP as the communication protocol for transmission between the image sending unit 270 and the receiving unit 340, the present invention is not limited thereto, and a special dedicated protocol may be used instead.

280 is an image display unit that displays captured images. 290 is an image recording unit that saves captured images within the X-ray image diagnostic apparatus 101.

Next, the configuration of the control apparatus 230 shall be described in detail.

232 is a main control unit. A central processing unit provided in the main control unit 232 manages various resources, such as buses, memories, and so on, the jobs and tasks of various control units, sequence control, and the like.

231 is an arm control unit that controls the arm driving unit 220 based on command signals from the main control unit 232.

233 is an input/output control unit that controls the settings input/output unit 240 based on command signals from the main control unit 232.

234 is an X-ray control unit that determines parameters necessary for irradiation (tube voltage, tube current, irradiation pulsewidth) for the X-ray emission unit 211 and controls the X-ray emission unit 211, based on command signals from the main control unit 232.

235 is an image processing control unit that calculates parameters for the various types of image processing performed by the image processing unit 250, controls the image processing sequences, and so on, based on command signals from the main control unit 232.

236 is a compression coding method selection unit that selects the compression coding method to be used by the compression coding unit 260 based on command signals from the main control unit 232. The compression coding method selection unit 236 also calculates parameters required by the compression coding unit 260 and sends those parameters to the compression coding unit 260.

237 is an image sending control unit that selects the communication protocol used when the image sending unit 270 communicates data, controls the flow of communication, and so on. The image sending control unit 237 also has functionality for monitoring the image sending unit 270, measuring the effective bandwidth for transmission, and obtaining measurement values.

<3. Configuration of Remote Control Apparatus>

Figure 3:
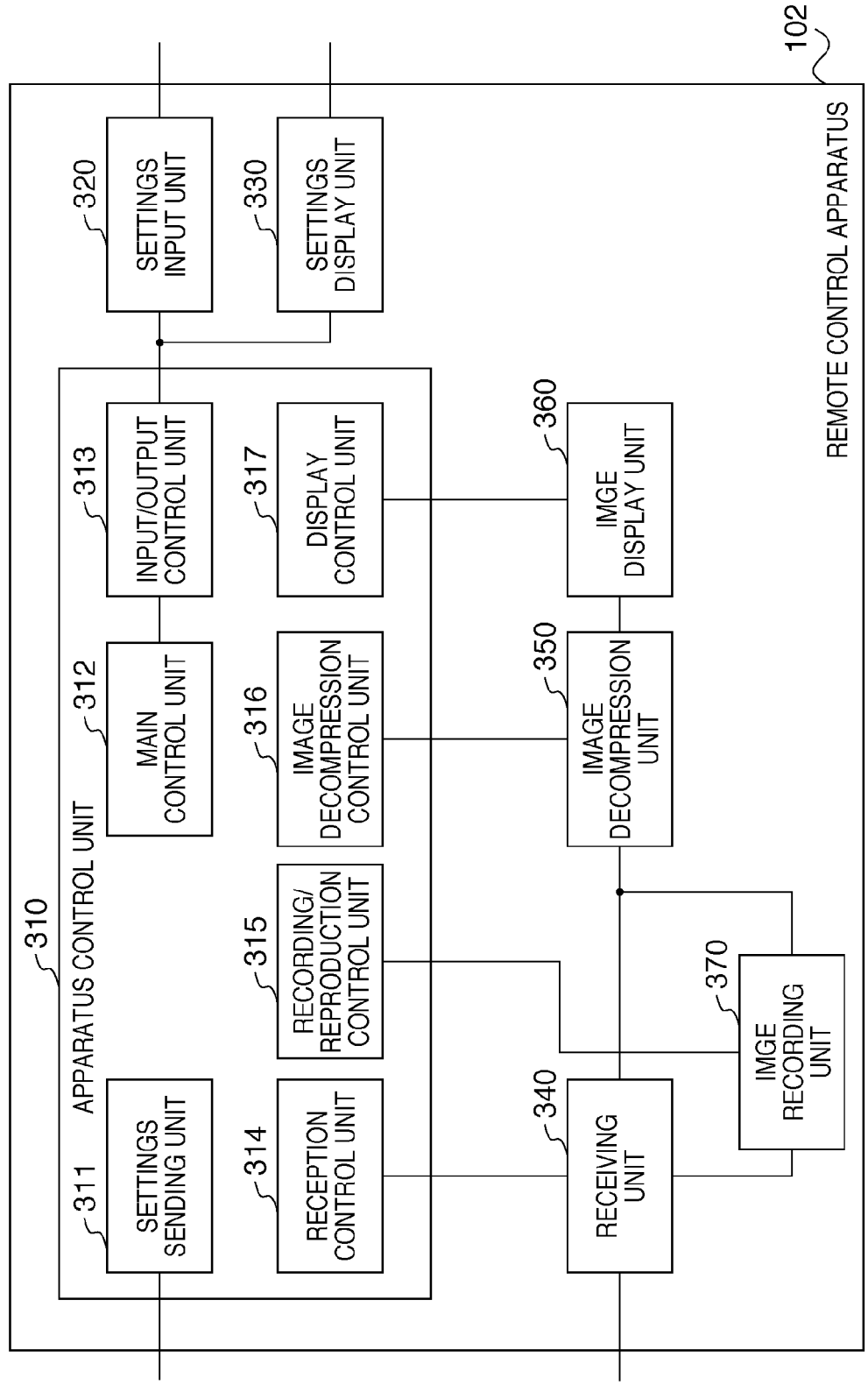
FIG. 3 is a diagram illustrating the internal configuration of a remote control apparatus 102.

Next, the remote control apparatus 102 shall be described using FIG. 3.

The remote control apparatus 102 is an apparatus by which an operator operates the X-ray image diagnostic apparatus 101 from a remote location, and FIG. 3 shows the internal configuration of the remote control apparatus 102.

In FIG. 3, 310 is an apparatus control unit that controls the overall remote control apparatus 102. The apparatus control unit 310 shall be described in detail later. 320 is a settings input unit that accepts settings from the operator. Like the settings input unit 241, the settings input unit 320 is realized using illuminated switches, a touch-panel liquid-crystal display, or the like. However, because the remote control apparatus 102 is in a different location than the X-ray image diagnostic apparatus 101, there is no need to maintain the cleanliness thereof, and thus the settings input unit 320 may also be realized using an input device such as a keyboard or the like.

330 is a settings display unit that displays setting values set through the settings input unit 320 or the status of the remote control apparatus 102.

340 is a receiving unit that receives captured images transmitted from the image sending unit 270. 370 is an image recording unit that records captured images received by the receiving unit 340. The image recording unit 370 may be realized using a magnetic disk such as a hard disk, a solid-state memory, or the like.

350 is an image decompression unit that decompresses captured images received by the receiving unit 340. The image decompression unit 350 is configured so as to be capable of processing captured images encoded through both lossless and lossy compression methods.

360 is an image display unit that displays the captured images decompressed by the image decompression unit 350. The image display unit 360 is realized using a liquid-crystal monitor having a resolution sufficient for displaying the decompressed captured images.

Next, the apparatus control unit 310 shall be described in detail.

312 is a main control unit that controls the various control units, such as 311, 313, and 317, as well as the resources (not shown) of the remote control apparatus 102, such as the CPU, memories, input/output devices, and so on.

313 is an input/output control unit that performs control for accepting inputs from the settings input unit 320 and displaying setting values in the settings display unit 330.

311 is a settings sending unit that transmits setting values accepted by the input/output control unit 313 to the X-ray image diagnostic apparatus 101.

314 is a reception control unit that controls the protocol of the receiving unit 340 based on command signals from the main control unit 312.

315 is a recording/reproduction control unit that controls recording or reproduction performed by the image recording unit 370, calculates parameters used during recording/reproduction, and so on, based on command signals from the main control unit 312.

316 is an image decompression control unit that selects the decompression method for the image decompression unit 350 and controls the image decompression unit 350 based on command signals from the main control unit 312.

317 is a display control unit that performs control for the image display unit 360 to display captured images based on command signals from the main control unit 312.

<4. Flow of Processing in X-Ray Image Diagnostic Apparatus>

Figure 4:
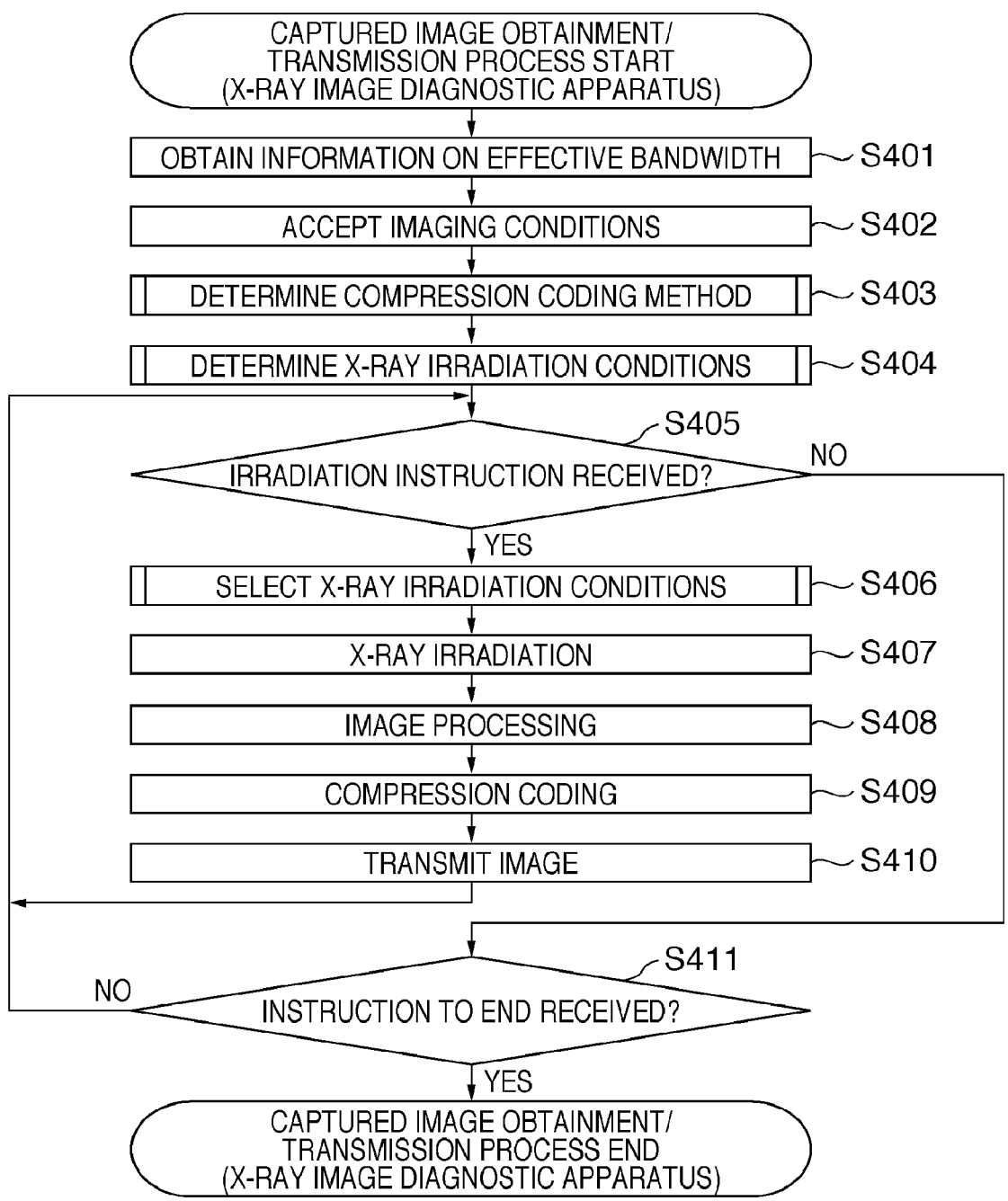
FIG. 4 is a flowchart illustrating the flow of a process by which the X-ray image diagnostic apparatus 101 obtains and transmits captured images.

Next, the flow of a process for obtaining and transmitting captured images, performed by the X-ray image diagnostic apparatus 101, shall be described using the flowchart in FIG. 4.

FIG. 4 is a flowchart illustrating the flow of a process by which the X-ray image diagnostic apparatus 101 obtains and transmits captured images.

In step S401, information regarding the effective bandwidth for transmission is obtained. In the present embodiment, the image sending control unit 237 monitors the flow control when the image sending unit 270 transmits data, and statistically calculates the effective bandwidth of the communication path (first calculation unit).

Although in the present embodiment, the effective bandwidth is calculated upon the X-ray image diagnostic apparatus 101 starting up, it should be noted that the present invention is not limited to such a setup; the configuration may be such that the effective bandwidth is calculated each time a captured image is transmitted. Furthermore, in cases where the effective bandwidth for transmission generally does not change, such as when the communication path uses a dedicated line, this step of calculating the effective bandwidth may be omitted, and a predetermined bandwidth may instead be pre-set.

In step S402, imaging conditions inputted by the operator are accepted. More specifically, in step S402, imaging conditions specified by the operator are accepted through the settings input/output unit 240 (obtainment unit). Data such as details of the diagnosis/treatment, the size of the captured image, the imaging time and framerate (the number of images captured obtained by imaging a subject multiple times over a certain unit of time), and so on can be given as examples of the imaging conditions that are accepted here.

In step S403, the compression coding method selection unit 236 selects the compression coding method. Note that the compression coding method is selected based on the effective bandwidth for transmission and imaging conditions obtained in steps S401 and S402. Note also that the imaging conditions used here are the size and frame rate of the captured image to be transmitted.

To be more specific, a combination of frames to be losslessly compressed and frames to be lossily compressed is determined so that the amount of data to be transmitted per unit of time falls within the effective bandwidth for transmission. Step S403 is executed by the main control unit 232; details of the process by which the main control unit 232 determines the stated combination (a compression coding method determination process) shall be described later using FIG. 5.

In step S404, the X-ray irradiation conditions are determined. Specifically, the X-ray irradiation conditions (tube voltage, tube current, irradiation pulsewidth) are determined based on the imaging conditions obtained in step S402 and information regarding the compression coding method combination as determined in step S403.

Note that when multiple compression coding methods have been determined in step S403, the same number of X-ray irradiation conditions as the number of compression coding methods are determined. Details of the process for determining the X-ray irradiation conditions shall be described later using FIG. 6.

In step S405, it is determined whether or not an instruction to irradiate has been received. Step S405 is executed by the main control unit 232, thus determining whether or not an instruction to irradiate has been inputted through the settings input unit 241 of the X-ray image diagnostic apparatus 101 or the settings input unit 320 of the remote control apparatus 102.

When it is determined in step S405 that an instruction to irradiate has been received, the process advances to step S406. However, when it is determined that an instruction to irradiate has not been received, the process advances to step S411.

In step S406, the X-ray irradiation conditions are selected. Step S406 is executed by the X-ray control unit 234, thus selecting, from the conditions determined in step S404, the X-ray irradiation conditions for a frame to be processed based on whether that frame is to be compressed losslessly or lossily. Details of the process for selecting the X-ray irradiation conditions shall be described later using FIG. 7.

In step S407, X-ray irradiation is executed. Step S407 is executed by the X-ray emission unit 211, and the timing of the irradiation and so on is controlled by the main control unit 232 and the X-ray control unit 234 based on the X-ray irradiation conditions selected in step S406. The X-rays irradiated in step S407 permeate the subject 201 and are detected by the X-ray imaging unit 212, thereby forming a captured image.

In step S408, the appropriate image processing is performed on the captured image that has been formed. Step S408 is executed by the image processing unit 250 under the control of the image processing control unit 235.

The image processing unit 250 performs the appropriate image processing based on information regarding whether the frame to be processed is to be losslessly or lossily compressed.

For example, when the frame is lossily compressed, a smoothing filter process is executed in order to increase the compression coding efficiency in later steps or to remove moirés.

Meanwhile, the X-ray amount selected in step S407 is set to be less for lossily-compressed frames than for losslessly-compressed frames, and thus the captured image has a narrow dynamic range. Thus a dynamic range correction process is executed.

The dynamic range correction process can, however, be performed by the remote control apparatus 102. In such a case, the data amount of lossily-compressed frames can be dropped by reducing the number of valid bits.

In step S409, a compression coding process is performed. Step S409 is executed by the compression coding unit 260 using the compression coding method determined in step S403. The compression coding method selection unit 236 specifies compression coding methods corresponding to losslessly-compressed frames and lossily-compressed frames, respectively, to the compression coding unit 260.

In step S410, the captured image is transmitted. The process of step S410 is executed by the image sending unit 270.

In step S411, it is determined whether or not an instruction to end processing has been received. The determination in step S411 is made by the main control unit 232 based on whether or not an instruction to end processing has been obtained by the settings input/output unit 240 from the operator.

When it is determined in step S411 that an instruction to end processing has been received, the X-ray image diagnostic apparatus 101 executes an ending procedure and stops its processing. However, when it is determined that an instruction to end processing has not been received, the process returns to step S405.

<5. Details of Processes in X-Ray Image Diagnostic Apparatus>

Details of the flow of processing performed in each of the steps that make up the captured image obtainment/transmission process performed by the X-ray image diagnostic apparatus 101 and described above using FIG. 4 shall be given hereinafter.

<5.1 Details of Compression Coding Method Determination Process (Step S403)>

Figure 5:
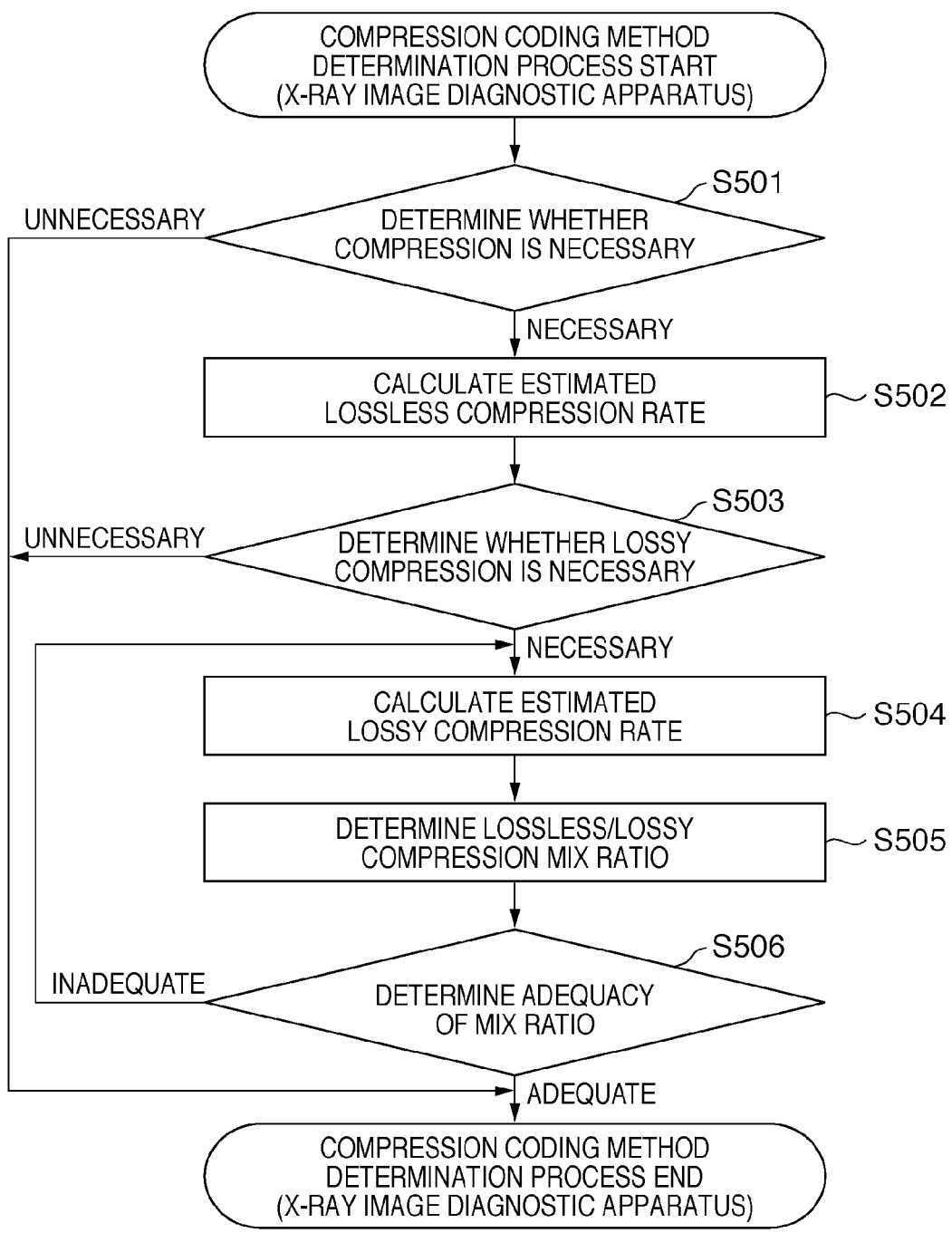
FIG. 5 is a flowchart illustrating the detailed flow of a compression coding method determination process (step S403).

First, the details of the compression coding method determination process (step S403) shall be described using FIG. 5.

FIG. 5 is a flowchart illustrating the detailed flow of the compression coding method determination process (step S403).

In step S501, it is determined whether or not it is necessary to encode the captured image with compression. Step S501 is executed by the main control unit 232. The main control unit 232 determines whether or not it is necessary to encode the captured image with compression based on the effective bandwidth for transmission obtained in step S401 and the imaging conditions obtained in step S402 shown in FIG. 4.

To be more specific, it is determined whether or not the inequality represented by the following Formula (1) holds true based on the effective bandwidth for transmission (transmission amount per unit of time) obtained in step S401 and the size per captured image, gradation of the captured image, and framerate (frames per second).

$$WE > S \times N \times F \quad (1)$$

In this formula, WE represents the effective bandwidth (bits per second), S represents the size (in pixels) of one frame of the captured image, N represents the gradation (in bits) of the captured image, and F represents the framerate (frames per second).

When the inequality expressed by Formula (1) holds true, it is determined that compression coding is unnecessary, and all the captured images are transmitted in an uncompressed state.

However, when the inequality expressed by Formula (1) does not hold true, the process advances to step S502.

In step S502, an estimated lossless compression rate (first compression rate) is calculated. Step S502 is executed by the compression coding method selection unit 236. The compression coding method selection unit 236 is provided with a dedicated storage region in which are stored profile images for each area of the subject. A profile image is a captured image having the highest possible resolution that the X-ray imaging unit 212 can obtain.

The compression coding method selection unit 236 selects the profile image appropriate for the area to be captured specified in step S402 in FIG. 4, and resamples the selected profile image at the size and gradation specified in step S401. A profile image that resembles the actual captured image is obtained in this manner.

The compression coding method selection unit 236 then instructs the compression coding unit 260 to encode the profile image, and the estimated lossless compression rate (first compression rate) is obtained based on the results of the encoding performed by the compression coding unit 260 (second calculation unit).

In step S503, it is determined whether or not lossy compression is necessary. Step S503 is executed by the main control unit 232. The main control unit 232 determines whether or not it is necessary to lossily compress the captured image based on the effective bandwidth for transmission WE obtained in step S401 of FIG. 4 and the estimated lossless compression rate obtained in step S502. Note that the estimated lossless compression rate is the post-compression data amount of the original image divided by the data amount of the original image, and is labeled as CR.

Whether or not lossy compression is necessary is determined through, for example, the following Formula (2).

$$WE > S \times N \times F \times CR \quad (2)$$

When the inequality in Formula (2) holds true, the compression coding method determination process ends. In this case, all the captured images are transmitted having been losslessly compressed.

However, when the inequality in Formula (2) does not hold true, the process advances to step S504.

In step S504, an estimated lossy compression rate (second compression rate) is calculated. Step S504 is executed by the main control unit 232. The main control unit 232 is provided with a dedicated storage region in which are stored profile images for each area of the subject. As mentioned before, a profile image is a captured image having the highest possible resolution that the X-ray imaging unit 212 can obtain. The main control unit 232 selects the profile image that most closely matches the imaging conditions (area, imaging angle, X-ray conditions, and so on) from the profile images and resamples the selected profile image at the size and gradation specified in step S402. A profile image that resembles the actual captured image is obtained in this manner.

The main control unit 232 instructs the compression coding unit 260, via the compression coding method selection unit 236, to lossily-compress the profile image obtained in step S504. The estimated lossy compression rate is then obtained based on the results of the encoding performed by the compression coding unit 260 (second calculation unit).

In step S505, the mix ratio for lossless and lossy compression is determined. Step S505 is executed by the main control unit 232. The main control unit 232 determines this ratio based on the effective bandwidth for transmission WE obtained in step S401 in addition to the estimated lossless compression rate (CR) calculated in step S502 and the estimated lossy compression rate calculated in step S504.

To be more specific, the number of losslessly-compressed frames (FR, hereinafter) and the number of lossily-compressed frames (FL, hereinafter) per unit of time are determined so that the following Formula (3) holds true. Note that the estimated lossy compression rate is the post-compression data amount of the original image divided by the data amount of the original image, and is labeled as CL.

$$WE > S \times N \times (CR \times FR + CL \times FL) \quad (3)$$

Note that F=FR+FL.

In step S506, the adequacy of the mix ratio of losslessly and lossily-compressed frames determined in step S505 is determined. The process of step S506 is executed by the main control unit 232. The main control unit 232 determines whether or not the estimated lossy compression rate CL (that is, the data loss) is adequate based on the imaging conditions obtained in step S402 of FIG. 4 and the combination of the number of losslessly-compressed frames FR and lossily-compressed frames FL obtained in step S505.

For example, when the mix ratio of losslessly-compressed frames FR is less than or equal to a predetermined threshold based on the imaging conditions, the mix ratio is determined to be inadequate, and the process returns to step S504. In this case, the estimated lossy compression rate CL is increased while increasing the number of losslessly-compressed frames FR, and the adequacy of the mix ratio is determined once again. However, when the mix ratio is greater than the predetermined threshold, it is determined to be adequate, and the compression coding method determination process ends.

<6. Detailed Flow of Processing in X-Ray Image Diagnostic Apparatus>

<6.1 Flow of X-Ray Irradiation Conditions Determination Process>

Next, the details of the X-ray irradiation conditions determination process (step S404) shall be described using FIG. 6.

FIG. 6 is a flowchart illustrating the detailed flow of the X-ray irradiation condition determination process (step S404).

In step S601, an irradiation amount for losslessly-compressed frame imaging is determined. The process of step S601 is executed by the X-ray control unit 234. The X-ray control unit 234 determines the tube voltage, tube current, and irradiation pulsewidth used when the X-ray emission unit 211 captures the losslessly-compressed frames FR based on the X-ray irradiation conditions set in step S402.

In step S602, an irradiation amount for lossily-compressed frame imaging is determined. The process of step S602 is executed by the X-ray control unit 234. The X-ray control unit 234 determines the tube voltage and tube current used when the X-ray emission unit 211 captures the lossily-compressed frames FL based on the tube voltage and tube current determined in step S601. The tube voltage (VL) determined in step S602 is a value that is less than the tube voltage (VR) determined in step S601.

In step S603, an irradiation time for lossily-compressed frame imaging is determined. The process of step S603 is executed by the X-ray control unit 234. The X-ray control unit 234 determines the irradiation pulsewidth used when the X-ray emission unit 211 captures the lossily-compressed frames FL based on the tube voltage and tube current determined in step S601 and the tube voltage and tube current determined in step S602.

The irradiation pulsewidth determined in step S603 is longer than that used for imaging losslessly-compressed frames, and the X-ray amount resulting from aligning that pulsewidth with the tube voltage and tube current determined in step S602 is adjusted to be less than or equal to the X-ray amount used for the losslessly-compressed frames FR.

<6.2 Flow of X-Ray Irradiation Conditions Selection Process>

Next, the details of the X-ray irradiation conditions selection process (step S406) shall be described using FIG. 7.

FIG. 7 is a flowchart illustrating the detailed flow of the X-ray irradiation condition selection process (step S406).

In step S701, the compression coding method is determined. The process of step S701 is executed by the main control unit 232. The main control unit 232 determines whether imaging has been performed using lossy or lossless compression based on the losslessly-compressed frames FR and the lossily-compressed frames FL determined in step S403, and notifies the X-ray control unit 234 thereof.

When it has been determined that the frame is a losslessly-compressed frame FR as a result of the determination performed in step S701, the process advances to step S702. In step S702, the X-ray control unit 234 determines an X-ray amount under the irradiation conditions corresponding to the losslessly-compressed frame FR (first irradiation condition).

However, when it has been determined that the frame is a lossily-compressed frame FL as a result of the determination performed in step S701, the process advances to step S703. In step S703, the X-ray control unit 234 determines an X-ray amount under the irradiation conditions corresponding to the lossily-compressed frame FL (second irradiation condition).

As described thus far, the X-ray image diagnostic apparatus 101 according to the present embodiment carries out efficient transmission using the effective bandwidth by combining losslessly-compressed frames and lossily-compressed frames based on the effective bandwidth for transmission and imaging conditions that have been set.

Imaging is carried out using a tube voltage and tube current set in accordance with the losslessly- and lossily-compressed frames. Furthermore, the configuration is such that the irradiation pulsewidth for lossily-compressed frames is longer than that for losslessly-compressed frames, thereby smoothing images through motion blur.

By capturing images over a long period of time at a low level of irradiation in such a manner, the compression rate during lossy compression can be improved, and high image quality can be obtained through noise reduction. Furthermore, because a higher X-ray amount than is required is not used when capturing lossily-compressed frames, the overall amount of radiation exposure can be reduced.

<7. Flow of Processing in Remote Control Apparatus>

Next, a process for displaying captured images, performed by the remote control apparatus 102, shall be described.

<7.1 Flow of Real Time Display Process>

Figure 8:
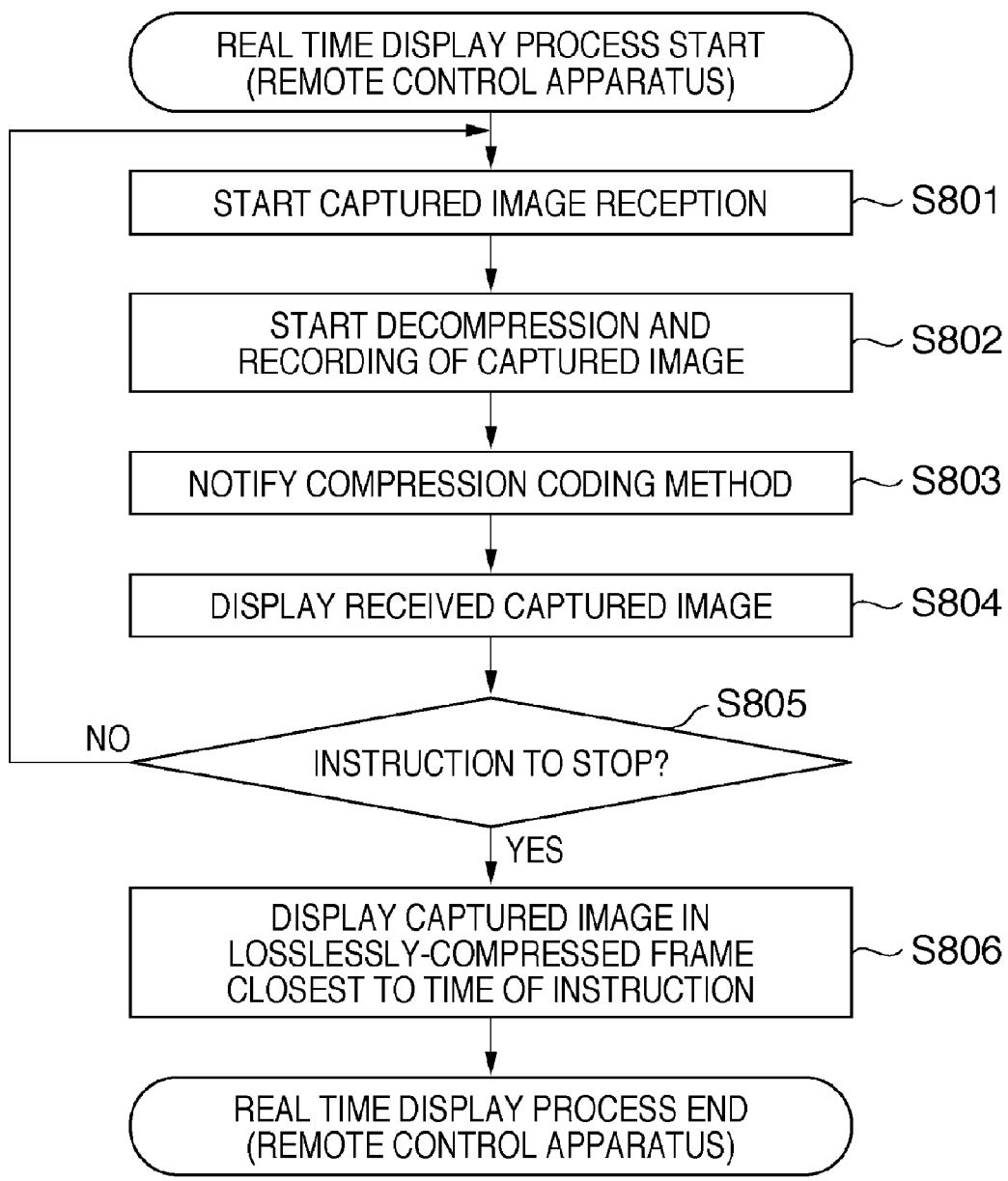
FIG. 8 is a flowchart illustrating the flow of a real time display process that displays captured images transmitted from the X-ray image diagnostic apparatus 101 in real time.

First, the flow of a real time display process that displays captured images transmitted from the X-ray image diagnostic apparatus 101 in real time shall be described using FIG. 8.

In step S801, the receiving unit 340 commences reception of a captured image transmitted by the X-ray image diagnostic apparatus 101.

In step S802, the captured image received by the receiving unit 340 is recorded into the image recording unit 370. At the same time, the captured image received by the receiving unit 340 is sent to the image decompression unit 350 in real time, and the image decompression unit 350 decompresses the image.

In step S803, the image compression control unit 316 is notified of whether the frame is a losslessly-compressed frame or a lossily-compressed frame, as determined by the image decompression unit 350 during decompression.

In step S804, the decompressed captured image is transmitted to the image display unit 360 and is displayed upon a display screen.

Here, the main control unit 312 continuously accepts inputs from the settings input unit 320 via the input/output control unit 313. Therefore, the process for receiving to displaying captured images (steps S801 to S804) is repeated until an instruction to stop the real time display of captured images is accepted by the input/output control unit 313 in step S805.

When an instruction to stop the real time display of captured images is accepted by the input/output control unit 313 in step S805, the main control unit 312 instructs the display control unit 317 to stop updating the captured image frames, and the process advances to step S806.

In step S806, the display control unit 317 ends the real time display process after controlling the captured image of the losslessly-compressed frame closest to the time at which the display control unit 31 accepted the instruction to stop updating the frames of the captured image in real time from the main control unit 312.

<7.2 Flow of Reproduction and Display Process>

Figure 9:
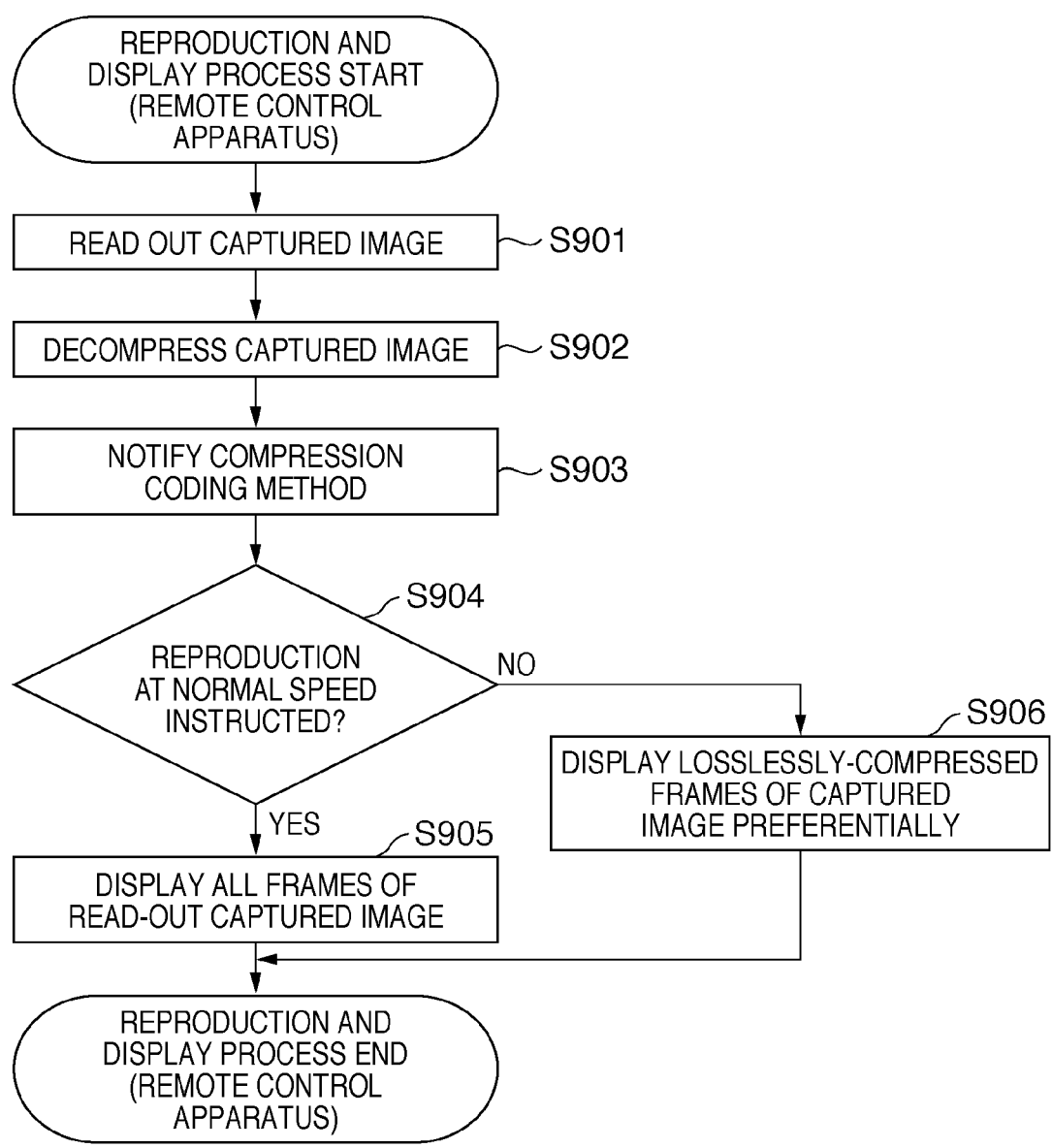
FIG. 9 is a flowchart illustrating the flow of a reproduction and display process that reproduces and displays captured images recorded in an image recording unit 370.

Next, the flow of a reproduction and display process that reproduces and displays captured images recorded in the image recording unit 370 shall be described using FIG. 9.

In step S901, a captured image recorded in the image recording unit 370 is read out in response to a reproduction instruction from the main control unit 312.

In step S902, the read-out captured image is sent to the image decompression unit 350, and the image decompression unit 350 performs the decompression process.

In step S903, the image decompression control unit 316 is notified of whether the frame is a losslessly-compressed frame or a lossily-compressed frame, as determined by the image decompression unit 350 during decompression.

In step S904, it is determined whether the reproduction and display process has been instructed to be performed at the normal speed (the same framerate as that used when imaging) when reproducing and displaying the captured image. When it is determined in step S904 that the reproduction and display process has been instructed to be performed at the normal speed, the process advances to step S905.

In step S905, the display control unit 317 sequentially displays all the frames of the multiple captured images that have been read out.

However, when it is determined in step S904 that the reproduction and display process has been instructed to be performed at a lower framerate than the normal speed (the framerate used when imaging) (in other words, when the number of images displayed per unit of time is less than the number of captured images), the process advances to step S906.

In step S906, when the display control unit 317 displays a number of the read-out captured images that corresponds to the specified framerate, captured images composed of losslessly-compressed frames are displayed preferentially. For example, when reproducing and displaying at a speed of less than or equal to five frames per second, only the losslessly-compressed frames are selected for display.

As described thus far, the present embodiment employs a configuration in which a combination of high-resolution captured images compressed losslessly and captured images compressed lossily at a high compression rate are transmitted within the effective bandwidth for transmission. Through this, it is possible to transmit captured images that have high resolution and a high framerate.

In addition, the present embodiment employs a configuration in which X-ray irradiation is performed differently depending on whether a frame has been losslessly compressed or lossily compressed. Through this, it is possible to reduce the amount of X-ray irradiation required for detection and diagnosis, making it possible to reduce the amount of radiation the patient is exposed to.

Furthermore, the present embodiment employs a configuration in which the remote control apparatus 102 displays all captured images when displaying the images in real time, but displays losslessly-compressed frames preferentially when reproducing and displaying recorded captured images. This makes it possible to make diagnosis using captured images that are always reproduced and displayed at high resolution.

Other Embodiments

The present invention may be applied to a system configured of a plurality of devices (e.g., a host computer, an interface device, a reader, a printer, and so on) or to an apparatus configured of a single device (e.g., a copy machine, a facsimile device, and so on).

Furthermore, it goes without saying that the object of the present invention can also be achieved by supplying, to a system or apparatus, a computer-readable storage medium in which the program code for software that realizes the functions of the aforementioned embodiment has been stored. In this case, the program code stored in the storage medium is loaded and executed by a computer (or CPU or MPU) of the system or apparatus, whereby the foregoing functions are achieved. In this case, the storage medium in which the program code is stored composes the present invention.

Examples of the storage medium that can be used to supply the program code include Floppy® disks, hard disks, optical disks, magneto-optical disks, CD-ROMs, CD-Rs, magnetic tape, non-volatile memory cards, ROMs, and so on.

However, the invention is not intended to be limited to the case where the functions of the aforementioned embodiments are implemented by a computer reading out the program code and executing the program code. It goes without saying that the present invention also includes the case where, for example, the OS (operating system) running on the computer performs part or all of the actual processing based on the instructions of the program code, and the functions of the above-described embodiment are implemented by that processing.

Furthermore, the case where the functions of the aforementioned embodiments are implemented after the program code read out from the storage medium has been written into a memory provided in a function expansion board installed in the computer or a function expansion unit connected to the computer is also included. That is, the case where after the program code has been written into a memory, a CPU or the like included in the function expansion board or the function expansion unit performs part or all of the actual processing based on the instructions of the program code, and the functions are implemented by that processing is also included.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-152258 filed Jun. 10, 2008, which is hereby incorporated by reference herein in its entirety.

What is claimed is:

1. An X-ray image diagnostic apparatus that irradiates a subject with X-rays and transmits multiple captured images obtained by imaging the subject to a control apparatus, the X-ray image diagnostic apparatus comprising:
a first calculation unit configured to calculate the transmission amount that can be transmitted per unit of time;
an obtainment unit configured to obtain conditions, out of the imaging conditions present when imaging the subject, that relate to the data amount of each captured image and the number of captured images captured per unit of time;
a second calculation unit configured to calculate the respective resulting data amounts when a captured image captured under the conditions obtained by the obtainment unit is compressed at first and second compression rates;
a determination unit configured to mix the captured images compressed using the first and second compression rates and determine the mix ratio so that the transmission amount per unit of time when the multiple captured images are transmitted is less than the transmission amount calculated by the first calculation unit; and a transmission unit configured to transmit the multiple captured images compressed using the first and second compression rates at the ratio determined by the determination unit.

2. The X-ray image diagnostic apparatus according to claim 1, wherein the first calculation unit calculates the transmission amount that can be transmitted per unit of time based on a measurement value obtained by measuring the effective bandwidth for transmission between the X-ray image diagnostic apparatus and the control apparatus.

3. The X-ray image diagnostic apparatus according to claim 1, wherein the first compression rate is the compression rate used when losslessly compressing the captured images, and the second compression rate is the compression rate used when lossily compressing the captured images.

4. The X-ray image diagnostic apparatus according to claim 3, wherein the determination unit determines the mix ratio by calculating FR and FL so that the inequality WE>S×N×(CR×FR+CL×FL) holds true, where S is the size of a single captured image, N is the gradation of the captured image, CR is the compression rate when losslessly compressing the captured image, CL is the compression rate when lossily compressing the captured image, FR is the number of captured images captured per unit of time that have been losslessly compressed, FL is the number of captured images captured per unit of time that have been lossily compressed, and WE is the transmission amount that can be transmitted per unit of time.

5. The X-ray image diagnostic apparatus according to claim 1, further comprising an X-ray control unit configured to control the X-ray amount when capturing images compressed at the first compression rate and the X-ray amount when capturing images compressed at the second compression rate.

6. The X-ray image diagnostic apparatus according to claim 5, wherein the X-ray control unit controls the X-ray amount so that the X-ray amount when capturing the captured images compressed at the greater of the first and second compression rates is less than the X-ray amount when capturing the captured images compressed at the lesser of the first and second compression rates.

7. An image processing method for an X-ray image diagnostic apparatus that irradiates a subject with X-rays and transmits multiple captured images obtained by imaging the subject to a control apparatus, the method comprising the steps of:

calculating the transmission amount that can be transmitted per unit of time;

obtaining conditions, out of the imaging conditions present when imaging the subject, that relate to the data amount of each captured image and the number of captured images captured per unit of time;

calculating the respective resulting data amounts when a captured image captured under the conditions obtained in the step of obtaining is compressed at first and second compression rates;

mixing the captured images compressed using the first and second compression rates and determining the mix ratio so that the transmission amount per unit of time when the multiple captured images are transmitted is less than the transmission amount calculated in the step of calculating the transmission amount; and transmitting the multiple captured images compressed using the first and second compression rates at the ratio determined in the step of mixing and determining.

8. A non-transitory computer-readable storage medium on which is stored a program for causing a computer to execute the image processing method according to claim 7.

* * * * *